United States Patent [19]

O'Keefe

[11] Patent Number: 4,833,265
[45] Date of Patent: May 23, 1989

[54] DATB AND ITS BIS-URETHAN

[75] Inventor: David M. O'Keefe, Mansfield, Tex.

[73] Assignee: Texas Explosives Co Inc, Mansfield, Tex.

[21] Appl. No.: 115,337

[22] Filed: Nov. 2, 1987

[51] Int. Cl.4 .............................................. C07C 79/46
[52] U.S. Cl. ..................................... 560/22; 564/393
[58] Field of Search ................... 560/22, 25; 564/393, 564/399

[56] References Cited

U.S. PATENT DOCUMENTS

| | | | |
|---|---|---|---|
| 2,679,538 | 5/1954 | Feuer et al. | 564/280 |
| 3,278,604 | 10/1966 | Hoffman et al. | 568/587 |
| 3,394,183 | 7/1968 | Dacons et al. | 564/399 |
| 3,847,990 | 11/1974 | Blahak | 564/393 |
| 3,933,886 | 1/1976 | Saygin | 560/22 |
| 4,227,007 | 10/1980 | Schirmer et al. | 560/22 |
| 4,282,369 | 8/1981 | Schirmer et al. | 560/25 |
| 4,600,797 | 7/1986 | Schossler | 514/393 |

FOREIGN PATENT DOCUMENTS 147119 4/1962 U.S.S.R. .
169504 3/1965 U.S.S.R. .

OTHER PUBLICATIONS

Noelting et al., Berichte der Deutschen Chemischen Gesellschaft vol. 17, pg. 260 (1884).
Barr, Berichte der Deutschen Chemischen Gesellschaft vol. 21, p. 1546 (1888).
Blanksma, Recueil des travaux chimiques des Pay-Bas vol. 21, p. 324 (1902).
Meisenheimer et al., Berichte der Deutschen Chemischen Gesellschaft vol. 39, p. 2540 (1906).
Blanksma, Recueil des travaux chimiques des Pay-Bas vol. 27, p. 56 (1908).
Korner et al., Atti della Reale Academia dei Lincei (Rendiconti) (5) vol. 17, p. 473 (1908).
Korner et al., Atti della Reale Academia dei Lincei (Rendiconti) (5) vol. 18, p. 101 (1909).
Feuer et al., Journal of The American Chemical Society vol. 72, pp. 2282-3 (1950).
Warman et al., Journal of Organic Chemistry vol. 26, pp. 2997-2998 (1961).
Siele et al., Journal of Organic Chemistry vol. 27, pp. 1910-1911 (1962).
Lorang, Recueil des travaux chimiques des Pay-Bas vol. 46, pp. 6325-652 (1927).

*Primary Examiner*—Bruce D. Gray

[57] ABSTRACT

The explosive 1,3-diamino-2,4,6-trinitrobenzene, commonly known as DATB, is prepred from m-phenylenediamine by making the bis-urethane m-phenylenediamine, nitrating this bis-urethane to the bis-urethane of DATB and removing the urethane groups from the DATB by solvolysis in sulfuric acid.

2 Claims, No Drawings

DATB AND ITS BIS-URETHAN

BACKGROUND OF THE INVENTION

1. Field of the Invention

This invention concerns the preparation of the bis-urethan of 1,3-Diamino-2,4,6-trinitrobenzene (DATB) [I] and the preparation of DATB [II] from its bis-urethan.

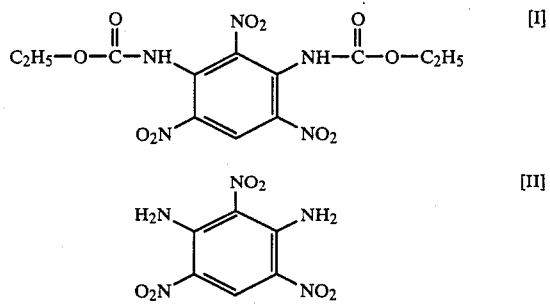

2. Background References

The following articles are cited as reference materials to the prior art of this invention:

(1) Noelting and Collin—Berichte der Deutschen Chemischen Gesellschaft, Vol. 17, 260 (1884).
(2) Barr—Berichte der Deutschen Chemischen Gesellschaft, Vol. 21, 1546 (1888).
(3) Blanksma—Recueil des Travaux chimiques des Pay-Bas, Vol. 21, 324 (1902).
(4) Meisenheimer and Patzig—Berichte der Deutschen Chemischen Gesellschaft, Vol. 39, 2540 (1906).
(5) Blanksma—Recueil des Travaux chimiques des Pay-Bas, Vol. 27, 56 (1908).
(6) Korner and Contardi—Atti della Reale Academia dei Lincei (Rendiconti) [5] Vol. 17, 473 (1908).
(7) Korner and Contardi—Atti della Reale Academia dei Lincei (Rendiconti) [5] Vol. 18, 101 (1909).
(8) Hass, Feuer, and Harban—Journal of The American Chemical Society, Vol. 72 pp 2282-3 (1950).
(9) Feuer and Harban—U.S. Pat. No. 2,679,538; May 25, 1954.
(10) Warman and Siele—Journal of Organic Chemistry, Vol. 26, pp. 2997-8 (1961).
(11) Orlova, Zhilin, Zbarskii, Maksimov, and Shutov—Russian Pat. No. 147,119; Apr. 28, 1962.
(12) Siele and Warman—Journal of Organic Chemistry, Vol. 27, pp. 1910-11, (1962).
(13) Shutov, Zhilin, Zbarskii, and Orlova—Russian Pat. No. 169,504; Mar. 17, 1965.
(14) Hoffman and McDonough—U.S. Pat. No. 3,278,604; Oct. 11, 1966.
(15) Dacons, Kamlet and Hoffsommer—U.S. Pat. No. 3,394,183; July 23, 1968.
(16) Lorang—Receil des Travaux chimiques des Pay-bas, Vol. 46, pp. 635-52, (1927).

3. Description of the Prior Art

The prior art teaches that given suitable substitution in the one and three positions of a 2,4,6-trinitrobenzene derivative, the compound will react with ammonia gas or alcoholic ammonia to replace the substituents in the one and three positions with the—$NH_2$ groups, giving the explosive, DATB, in Equation (1).

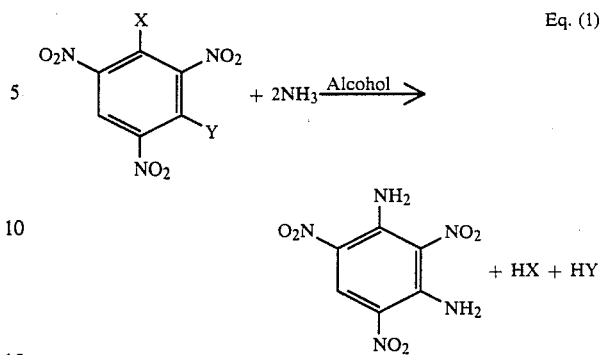

In Equation (1), X and Y may be halogens or ethers or a mixture (i.e.—X may be a halogen and Y an ether.) This is the teaching of references 1 thru 15, save only reference 4. This Equation (1) in one or another of its variations is the common route by which the explosive DATB is prepared.

Reference (4) presents the curious reaction of Equation (2).

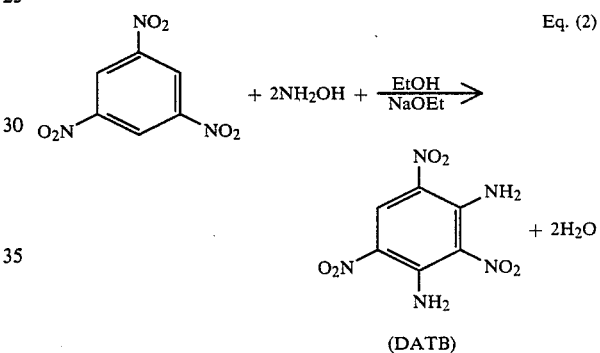

Intuitively, one would not expect a high yield of DATB from Equation (2). As previously mentioned, references 1 thru 15 have the three nitro groups in place on the benzene ring before the amino groups ($NH_2$) are introduced. Only reference 16 reverses this procedure. In reference 16, Lorang studied the reactions of polynitroaromatic N-nitroureas, such as [III] which he made by equation (3).

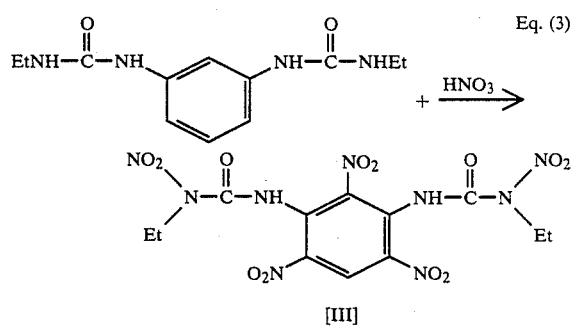

Note that [III] is not only a polynitroaromatic compound, but it is also a double nitramine and would be expected to be somewhat hazardous. Lorang heated [III] with $H_2O$ and obtained DATB; he also heated [III] with alcohol to make the bis-urethan of DATB [I] as in equation (4):

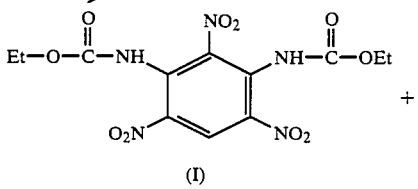

Lorang then reacted (I) with alcoholic ammonia to make 1,3-Diamino-2,4,6-trinitrobenzene (DATB).

SUMMARY OF THE INVENTION

It is the purpose of this invention to make the bis-urethan of 1,3-Diamino-2,4,6,-trinitrobenzene (DATB) (I) and from (I) to make the explosive DATB by a method which does not involve the hazardous double nitramine of Lorang. Toward this end, we make the bis-urethan of m-phenylenediamine (IV) by reaction of the amine with a chloroformate ester as in equation (5):

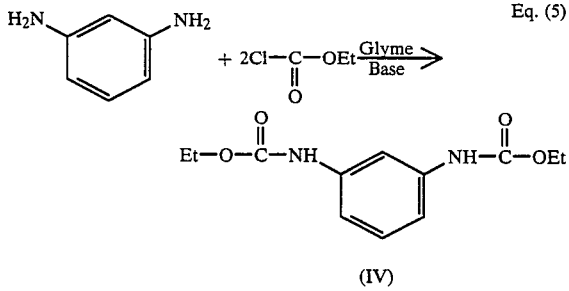

This is then followed by a low temperature trinitration of (IV) to make (I) directly. Note that (IV) is not an explosive and that (I) is not a nitramine.

This invention also provides a convenient method converting (I) to 1,3-Diamino-2,4,6-trinitrobenzene (DATB): warming (I) in concentrated sulfuric acid followed by drowning the solvolysis mixture in ice water. Although the product, DATB, is soluble in sulfuric acid, it is not oxidized or degraded by this procedure.

DESCRIPTION OF THE PREFERRED METHODS

The method of this invention may be practiced by carrying out the following specific procedures.

PROCEDURE 1.

Preparation of the Bis-urethan of m-Phenylenediamine 10.8 gms of m-phenylenediamine (0.1 mole) is dissolved in 100 ml of methanol and 10.6 gms of solid sodium carbonate (0.1 mole) is added. This stirred slurry is then cooled in ice water. Over a 45 minute period a solution of 21.6 gms of ethyl chloroformate (0.2 moles) in 25 ml of ethylene glycol dimethyl ether is added dropwise to the m-phenylenediamine solution. The reaction is stirred for 1 hour after the addition is completed and the resulting pink slurry is poured into 1 liter of ice water. The precipitated urethan is filtered, washed well with water and set out to dry. The yield is 18.3 gms, (72%) of almost white powder which melts at 142°-6° C. Recrystallization from chloroform using Carbon black gives a white powder of unchanged melting point.

Procedure 2.

Preparation of the bis-urethan of 1,3-Diamino-2,4,6-trinitrobenzene, (DATB)

12.6 gms of the bis-urethan of m-phenylendiamine is dissolved in 50 ml of concentrated sulfuric acid, keeping the temperature below 10° C. The material is slow to dissolve, but no $CO_2$ evolution is noticeable. A nitration mixture is made up of 100 ml of 30% fuming sulfuric acid and 150 ml of 90% nitric acid; this nitration mixture is cooled below 10° C. Keeping the reaction temperature below 10° C, the cold urethan solution is added in small portions to the stirred nitration mixture. The exotherm on addition of the urethan is small. On completion of addition of the urethan solution, the stirred reaction is allowed to warm up slowly in its cooling bath. In 1.5 hours, the yellow reaction mixture is up to 24° C. At this point, it is quenched in 1 liter of crushed ice, the product filtered, washed well with water and set out to dry.

The apparently dry crumbly product amounted to over 100% of theory. It melted at 193°-8° C. Recrystallization from acetone/ethanol solution using carbon black gave 13.8 gms of white fluffy crystals (in two crops), melting at 225°-8° C. This is a 71% yield in the nitration.

PROCEDURE 3.

Preparation of DATB from its Bis-urethan

A preliminary attempt to solvolyze the bis-urethan by stirring it with trifluoroacetic acid at room temperature failed; the urethan was recovered with only mechanical losses, after one week at room temperature.

While the bis-urethan of DATB is readily soluble in concentrated sulfuric acid at room temperature, it is only slowly solvolyzed at room temperature and at 50° C. The following procedure gives a clean reaction. 2 gms of the bis-urethan of DATB is dissolved in 50 ml of concentrated sulfuric acid and stirred for 3 hours at 70°-73° C. Bubbles are evolved and the solution slowly turns a deep red color. After cooling, the solution is quenched in 400 ml of ice water and the yellow precipitate is filtered and washed with water. After drying, the product melts at 279°-81° C. and a mixture of this material with DATB (prepared from 1,3-dichloro-2,4,6-trinitrobenzene and ammonia) melts at 278°-81° C. The solvolysis yield is about 60%.

PROCEDURE 4. Stability of DATB in Sulfuric Acid

As a check on the stability of DATB in sulfuric acid under these conditions, 2 gms of DATB (prepared from 1,3-dichloro-2,4,6-trinitrobenzene and alcoholic ammonia) was stirred in 50 ml of concentrated sulfuric acid for 3 hours at 70°-3° C. The DATB readily dissolves; the initial bright orange color becomes red in time. After three hours, the solution is cooled and poured over 500 ml of chipped ice and the bright yellow solid is filtered, washed with water and set out to dry. The melting point of the recovered DATB is 277°-80° C. and the recovery was 2.0 gms, 100%. It is apparent that rather than degrading the DATB, sulfuric acid can be used as a solvent for it, i.e.—reclaiming DATB from PBX wastes and the like.

I claim:

1. The process of preparing a bis(ethyl)urethane of 1,3-diamino-2,4,6-trinitrobenzene consisting of reacting meta-phenylenediamine with ethyl chloroformate in the presence of a base to prepare the corresponding bis-(ethyl)urethane and then trinitrating said bis-(ethyl)urethane of 1,3-diamino-2,4,6-trinitrobenzene.

2. The process of preparing the explosive 1,3-diamino-2,4,6-trinitrobenzene, commonly known as DATB, from its corresponding bis(ethyl)urethane by heating said bis-(ethyl)urethane in sulfuric acid for three hours at a temperature of 70°–73° C., quenching the solvolysis mixture in ice and isolating the DATB thus prepared.

* * * * *